(12) United States Patent
Bjorncrantz

(10) Patent No.: US 9,333,229 B2
(45) Date of Patent: May 10, 2016

(54) WINTERIZED CRUDE CANNABIS EXTRACTS AND METHODS OF PREPARATION AND USE

(71) Applicant: William Bjorncrantz, Stevensville, MI (US)

(72) Inventor: William Bjorncrantz, Stevensville, MI (US)

( * ) Notice: Subject to any disclaimer, the term of this patent is extended or adjusted under 35 U.S.C. 154(b) by 114 days.

(21) Appl. No.: 14/225,254

(22) Filed: Mar. 25, 2014

(65) Prior Publication Data

US 2015/0105455 A1  Apr. 16, 2015

Related U.S. Application Data

(60) Provisional application No. 61/891,764, filed on Oct. 16, 2013.

(51) Int. Cl.
| | | |
|---|---|---|
| *A01N 65/00* | (2009.01) | |
| *A61K 36/185* | (2006.01) | |
| *A61K 31/05* | (2006.01) | |
| *A61K 31/353* | (2006.01) | |
| *A61K 31/192* | (2006.01) | |
| *A24F 47/00* | (2006.01) | |
| *A61K 9/00* | (2006.01) | |

(52) U.S. Cl.
CPC ............. *A61K 36/185* (2013.01); *A24F 47/008* (2013.01); *A61K 9/007* (2013.01); *A61K 31/05* (2013.01); *A61K 31/192* (2013.01); *A61K 31/353* (2013.01); *A61K 2236/00* (2013.01)

(58) Field of Classification Search
CPC ....................................................... A61K 36/00
USPC ........................................................... 424/725
See application file for complete search history.

(56) References Cited

U.S. PATENT DOCUMENTS

| | | |
|---|---|---|
| 6,946,150 B2 | 9/2005 | Whittle |
| 7,344,736 B2 | 3/2008 | Whittle et al. |
| 8,435,556 B2 | 5/2013 | Stinchcomb et al. |
| 8,449,908 B2 | 5/2013 | Stinchcomb et al. |
| 2002/0136752 A1 | 9/2002 | Whittle et al. |
| 2010/0012118 A1 | 1/2010 | Storz |
| 2011/0021617 A1 | 1/2011 | Korthout et al. |
| 2011/0256245 A1 | 10/2011 | Rosenblatt et al. |
| 2011/0277756 A1 | 11/2011 | Terry et al. |
| 2013/0274321 A1 | 10/2013 | Newland |

FOREIGN PATENT DOCUMENTS

| | | |
|---|---|---|
| WO | 02/064109 A2 | 8/2002 |

OTHER PUBLICATIONS

Verso User Manual, dated Sep. 4, 2013, pp. 1-9.

*Primary Examiner* — Michael Meller
(74) *Attorney, Agent, or Firm* — Michael Harlin

(57) ABSTRACT

The present technology relates to liquid compositions for use in a personal vaporizer. More particularly, the present technology relates to liquid compositions comprising winterized *Cannabis* extract, and to methods of administering vaporized winterized *Cannabis* extract to a subject by inhalation.

4 Claims, No Drawings

US 9,333,229 B2

WINTERIZED CRUDE CANNABIS EXTRACTS AND METHODS OF PREPARATION AND USE

CROSS-REFERENCE TO RELATED APPLICATIONS

This application claims benefit of priority to U.S. Provisional Patent Application No. 61/891,764, filed on Oct. 16, 2013, the disclosure of which is incorporated herein by reference.

FIELD OF THE INVENTION

The present technology relates to liquid compositions for use in a personal vaporizer. More particularly, the present methods relate to liquid compositions prepared by removing waxy ballast from crude *Cannabis* extracts by a process of winterization and the use of those liquid compositions in personal vaporizers. This liquid composition comprises at least one *Cannabis* extract, and optionally a co-solvent and other components.

BACKGROUND OF THE INVENTION

Personal vaporizers are devices that turn a liquid into a vapor so that a person can inhale the vapor. Many personal vaporizers are relatively small (pocket-sized or pen-sized), battery-powered, and use an atomizer or heater to vaporize the liquid. The personal vaporizer converts a liquid into a vapor that is inhaled. Personal vaporizers are inherently portable and come in a variety of forms.

An exemplary personal vaporizer is found in the Pen Kits available from Verso PV of Fort Collins, Colo. Pictures and instructions for use of the Verso personal vaporizer are shown in Appendix A. Additional examples of commercially available personal vaporizers include the liquid personal vaporizers from Atmos; the vaporizer pen from VapeToys, O.pen-VAPE and many others. Personal vaporizers include electronic flameless vapor inhaler units that may simulate a cigarette.

Personal vaporizers are often used as alternatives to smoked tobacco products, such as cigarettes, cigars, or pipes. Inhaled doses of vapor provide a physical sensation similar to smoking. However, because a personal vaporizer is typically electrically powered, no tobacco, smoke, or combustion is usually involved in its operation. For portability, and to simulate the physical characteristics of a cigarette, cigar, or pipe, a personal vaporizer may be battery powered. In addition, a personal vaporizer may be loaded with a nicotine bearing substance and/or a medication bearing substance. The personal vaporizer may provide an inhaled dose of nicotine and/or medication by way of the heated and atomized substance. Thus, personal vaporizers are sometimes referred to as electronic cigarettes, or e-cigarettes. However personal vaporizers are not limited to delivering nicotine or acting as a cigarette substitute. To the contrary, they may be used to administer flavorants, medicinal agents, or other substances that are vaporized and then inhaled.

Personal vaporizers can be filled with liquid compositions to be vaporized. Such liquid compositions generally include a liquid base and one or more other components. Typical personal vaporizer liquid bases include propylene glycol, glycerol, or PEG-400, and they are primarily intended to function with the addition of water-soluble additives.

Besides delivering nicotine or being used as a cigarette substitute, personal vaporizers have been used to provide a vapor from solutions of actives (such as ingredients, flavors and/or medicinal compounds) in a base of propylene glycol, which is the standard liquid base for e-cigarettes. Propylene glycol is non-toxic and safe for daily consumption. When heated, propylene glycol produces a smooth vapor, when inhaled, with a mildly sweet taste. When a solution of propylene glycol, actives, and flavorings are mixed and heated, the vapor becomes infused with the added ingredients, taking on a variety of flavors and therapeutic uses. Ingredients such as nicotine and flavorings such as "Peach Flavor" from LorAnn Oils have been used in liquid compositions for personal vaporizers.

However manufacturers of personal vaporizer liquids have had difficulty creating a stable emulsion containing oil-soluble compounds. The personal vaporizer liquids presently on the market typically have an off palate and/or do not perform well, due to a waxy ballast discharge, terpenoid loss, separation from base liquid, the presence of self-emulsifying agents creating a range of viscosity, and unstable and unrefined emulsions, respectively. Other emulsifiers will thermally decompose and produce carcinogenic byproducts with intolerable flavor.

Personal vaporizers can also be used for the delivery of cannabinoids or *cannabis* extracts. The National Institutes of Health (NIH) released a review of the scientific data concerning potential therapeutic uses for marijuana in 1997. In that review, the NIH found that marijuana may have beneficial medicinal effects and recommended that researchers develop alternative dosage forms for the drug, such as a "smoke free" inhaled delivery system. Various studies have documented therapeutically beneficial medicinal uses of the major active component of marijuana, delta-9-tetrahydrocannabinol (THC). See U.S. Pat. No. 6,713,048, entitled "$\Delta^9$ tetrahydrocannabinol ($\Delta^9$ THC) solution metered dose inhalers and methods of use". Makers of personal vaporizer liquids containing oil-soluble compounds, or resins, have had difficulty creating a stable emulsion. The personal vapor liquids presently on the market typically have an off palate and/or do not perform well, primarily due to a waxy ballast discharge, separation from base liquid, the presence of self-emulsifying agents creating a range of viscosity, and unstable and unrefined emulsions.

WO 02/064109 discloses a method of preparing an extract from medicinal *cannabis*. The process comprises (1) a heating step to decarboxylate the acid form of the cannabinoids to their neutral form; (2) a first extraction with a specified volume of liquid carbon dioxide for 6-8 hours; and (3) a step to reduce the proportion of non-target materials, referred to as winterization, which precipitates out waxes. More specifically, step (1) comprises heating chopped *cannabis* at 100-150° C. for sufficient time to allow decarboxylation. Step (2) comprises CO2 extraction using supercritical conditions. Step (3) comprises conducting an ethanol precipitation at −20° C. for 24 hours and removing the waxy material by filtration.

U.S. Pat. No. 6,946,150 describes formulations containing cannabinoids for administration via a pump action spray. In particular, the invention relates to pharmaceutical formulations, for use in administration of lipophilic medicaments via mucosal surfaces, comprising: at least one lipophilic medicament, a solvent and a co-solvent, wherein the total amount of solvent and co-solvent present in the formulation is greater than 55% wt/wt of the formulation and the formulation is absent of a self emulsifying agent and/or a fluorinated propellant.

U.S. Pat. No. 7,344,736 also describes extraction of cannabinoids from *cannabis* using liquid carbon dioxide, as well as winterization to remove waxy material. The patent relates preparation of a botanical drug substance (BDS) for incorporation into a medicament. It also relates to a BDS of given purity, for use in pharmaceutical formulations. In particular it relates to BDS comprising cannabinoids obtained by extraction from *cannabis*. For example, the patent discusses an extraction process where a botanical raw material is decarboxylated by heating to approximately 105° C. for 15 minutes, followed by approximately 145° C. for a minimum of 55 minutes for THCA and 90 minutes for CBDA. An extraction with food grade liquid carbon dioxide (CO2) for up to 10 hours at a pressure of approximately 60 bar+/−10 bar and 10° C.+/−5° C. The CO2 is removed by depressurization to recover crude extract. A "Winterization" step is performed in which the crude extract is dissolved in ethanol followed by chilling solution (−20° C.+/−5° C. for up to 52 hours) to precipitate unwanted waxes. The unwanted waxy materials are then removed by cold filtration using a 20 μm (micron) filter. Ethanol and water are removed from the filtrate by thin film evaporation under reduced pressure (60° C.+/−2° C., with vapor at 40° C.+/−2° C./172 mbar and 72 mbar+/−4 mbar). This yields the botanical drug substance.

SUMMARY OF THE INVENTION

The present compositions and methods provide a new and improved method for refining crude *cannabis* extract(s) using winterization to create a personal vaporizer liquid with high-purity and stability, for use in a personal vaporizer. The present compositions and methods are superior in quality, and performance with respect to existing personal vaporizer liquids containing *Cannabis* extracts. The present compositions and methods solve the problem of providing *Cannabis* extracts for use in a personal vaporizer, without causing thermal decomposition products or without affecting the taste and potency of the vaporized material, by removing waxy ballast material from the extracts.

As one aspect of the present invention, a liquid composition is created through "winterization" of crude *cannabis* extracts for use with a personal vaporizer. The *Cannabis* extracts remain pharmacologically active after winterization. In some embodiments, a liquid composition for a personal vaporizer comprises a winterized *cannabis* extract; a liquid co-solvent; and the composition has less than 1% by weight of waxy ballast. Alternatively, the liquid composition is essentially free of components that burn, smoke or decompose at temperatures employed in a personal vaporizer. For example, the liquid composition may be essentially free of components that burn at a temperature in the range of about 340° to about 390° F., alternatively free of components that burn at a temperature in the range of about 170° to about 200° C., alternatively free of components that burn at a temperature in the range of about 171° to about 198° C. Alternatively, the liquid composition is essentially free of one or more of wax esters, glycerides, unsaturated fatty acids, and preferably it is essentially free of each of them. In some embodiments, the liquid composition further comprises one or more emulsifiers; in other embodiments, the liquid composition is essentially free of added emulsifiers.

As another aspect of the present invention, a method of preparing a liquid composition for a personal vaporizer is provided. The method can comprise providing a crude *Cannabis* extract; winterizing the crude *Cannabis* extract, such as by chilling to a temperature equal to or less than 0° C., alternatively, equal to or less than about −20° C., for a period equal to or greater than 1 hour; and combining the winterized *Cannabis* extract with a liquid base. The method can also include forming a crude *Cannabis* extract by extracting cannabinoid compounds from a *Cannabis* plant. The method can also include adding other components for a personal vaporizer liquid, such as a flavorant, humectant, or anti-oxidant.

As yet another aspect of the present invention, a method of administering vaporized cannabinoid compounds to a subject by inhalation is provided. The method comprises vaporizing a liquid composition in a personal vaporizer, wherein the liquid composition comprises a winterized *Cannabis* extract. The liquid composition can further include a co-solvent, for example in an extract:co-solvent ratio between 5:1 and 1:5, alternatively in a ratio between 200:1 and 1:200. Preferably the liquid composition is essentially free of components that burn or smoke at temperatures employed in a personal vaporizer. The method can further comprise dispensing the vaporized winterized *Cannabis* extract through a mouthpiece of the personal vaporizer, and inhalation of the vaporized winterized *Cannabis* extract. The method can also comprise treating a disease, disorder or condition with the vaporized winterized *Cannabis* extract.

As yet another aspect of the present invention, a container is provided for holding a liquid composition comprising a winterized *cannabis* extract and a liquid base suitable for vaporization and inhalation, wherein the container is adapted for attachment to a personal vaporizer.

As another aspect of the present invention, a kit is provided which comprises a personal vaporizer, dispensary vessels, a battery charger, and a container holding a liquid composition adapted for use in a personal vaporizer.

As another aspect of the present invention, a method is provided for administering a liquid composition comprising a winterized *cannabis* extract, and optionally comprising a co-solvent, such as propylene glycol. Suitable liquid compositions can be made at a range of known or targeted therapeutic cannabinoid ratios. The method comprises vaporizing any of the liquid compositions described herein in a personal vaporizer. The method can also include dispensing the winterized *cannabis* extracts through a mouthpiece of the personal vaporizer. The method can also include inhalation of the vaporized winterized *cannabis* extracts with the optional addition of a co-solvent. Where the vaporized *cannabis* extracts are a medicinal agent, the method can also include treating a disease, disorder or condition with the vaporized *cannabis* extracts using methods and components listed below.

As further aspects of the present invention, a container holding a liquid composition for a personal vaporizer is provided. The container holds a liquid composition that includes a *Cannabis* extract suitable for vaporization and inhalation. The liquid composition is made from a winterized *cannabis* extract, optionally with a co-solvent (propylene glycol), in various ratios of co-solvent to *Cannabis* extract. The liquid composition is stable and can include other components. The container is adapted for attachment to, or is part of a personal vaporizer.

Various embodiments are disclosed of the foregoing aspects of the present invention. In any of those aspects, the liquid can be a composition entirely of refined crude *cannabis* extracts, a combination of refined *cannabis* extracts, or a liquid composition of one or more refined *cannabis* extracts with the use of a co-solvent, such as propylene glycol. Preferably, the composition is essentially free of ethanol or other solvents used for initial extraction or for winterization.

In a liquid composition suitable for use in a personal vaporizer, the one or more refined *cannabis* extracts with and without the addition of a co-solvent, can include a flavorant or an additional medicinal agent.

DETAILED DESCRIPTION

The present technology can be employed in any personal vaporizer where a liquid composition can be loaded into the personal vaporizer and inhaled as a vapor. The liquid composition is created through winterization of a crude *Cannabis* extract or by a process including single or multiple extractions to prepare a winterized *Cannabis* extract from a *Cannabis* plant.

The term "*Cannabis* plant" encompasses wild type *Cannabis sativa*, *Cannabis indica*, *Cannabis afghanica*, and other variants thereof, including *cannabis* species which naturally contain different amounts of the individual cannabinoids. Also included are *Cannabis* subspecies and plants which are the result of genetic crosses, self-crosses or hybrids thereof. Also included are hemp plants. The term "*Cannabis* extract" is to be interpreted accordingly as encompassing material extracted from one or more *cannabis* plants.

The preparation of the crude *Cannabis* extracts can be done with a solvent of choice, as the secondary extraction (or winterization) ensures the release and removal of any trapped or residual solvents. Solvents of choice for the initial extraction are those of high-purity with no odor-additives, and may be used in combination. Solvents like $CO_2$, n-butane, iso-butane, propane, water and ice, some used under sub-critical or super-critical conditions or within a closed recycling system.

The crude *Cannabis* extract can be obtained by any suitable technique for separating *cannabis* resin from the plant. The extract can be obtained by simply shaking or scraping resin off a *Cannabis* plant. Alternatively, crude *Cannabis* extract can be provided in the form of hashish. As another alternative, butane or carbon dioxide can be used as a solvent for the extraction technique. As an example, the *Cannabis* plant is dried and ground into fine material. The ground material is mixed with a food-grade alcohol (such as at a ratio of 1 lb of ground material to 1.5 gallons of alcohol), so that the ground material is fully immersed in the alcohol. The mixture is then placed in a covered container and heated for 3 hours at 190° F., while refluxing the alcohol so as to distill the oils from the ground material. After allowing the mixture to cool, it is passed through a strainer to separate liquid from solid plant residue. The liquid is then separated such as by pouring through a filter. The filtered liquid contains alcohol and *Cannabis* extract. In order to remove the alcohol, the filtered liquid is subjected to an evaporative process such as heating, which leaves the *Cannabis* extract behind.

THC and CBD are the main medicinally active constituents in *Cannabis*. However, these constituents are present as the biologically inactive carboxylic acids in *Cannabis* plants. When extracting THC or CBD from *cannabis* plants, it has been the practice to convert the storage precursor compounds of THCA and CBDA into their more readily extractable and pharmacologically active forms. THC and CBD acids slowly decarboxylate over time, and applying heat increases the rate of decarboxylation. When the cannabinoid compounds are included in a liquid composition for a personal vaporizer, it may not be necessary to convert THCA and CBDA into THC and CBD prior to use, since the personal vaporizer supplies heat. In other words, the crude *Cannabis* extracts used in the present processes may be obtained by low-temperature (below 60° C., alternatively below 45° C., alternatively below 18° C.) extraction techniques.

The winterization process retains the more polar cannabinoid molecules while ridding the crude extract of most other waxes, which is often referred to as waxy ballast. The secondary extraction or "winterization" is an ethanolic-precipitation for removing waxy ballast and purifying the crude *Cannabis* extract of wax esters, glycerides, and unsaturated fatty acids, which hinder the extract from a refined, liquid state. "Winterization" releases any trapped solvents from the initial extraction from the extremely viscous crude extracts. After "winterization", the refined *Cannabis* extract is in liquid form, ready for use in a personal vaporizer, with no co-solvents or emulsifiers needed. Alternatively, the refined *Cannabis* can be combined with a liquid base and/or co-solvent and/or one or more emulsifiers.

The process of removing waxy ballast from crude *cannabis* extract using "winterization", involves chilling the crude *Cannabis* extract to a temperature less than or equal to about 0° C., alternatively less than or equal to below about −10° C., alternatively less than or equal to below about −20° C. for a time period. The time period may be at least 1 hour, alternatively at least about 24 hours, alternatively at least about 48 hours, alternatively at least about 60 hours, alternatively at least about 72 hours. After the chilling freezing period, the crude *Cannabis* extract can be cold-filtered to remove waxy ballast. For example, a Whatman #1 lab filter with vacuum assist is initially used to remove the material that is insoluble, and secondly the crude extract is run through syringe filters (for example, 0.45 or 0.2 micron filters), which takes out any remaining plant material, as well as any bacteria present.

The *Cannabis* extract contains one or more of the following cannabinoid compounds: cannabidiol (CBD), delta-9-tetrahydrocannabinol (THC), cannabidiolic acid (CBDA), tetrahydrocannabinolic acid (THCA), cannabinol (CBN), cannabichromene (CBC), cannabigerol (CBG), delta-8-THC (Δ8-THC), tetrahydrocannabivarin (THCV), or a combination thereof. Alternatively, one or more synthetic cannabinoids (e.g., HU-210) can be added to the crude *Cannabis* extract or to the refined *Cannabis* extract.

The *Cannabis* extract may also include non-cannabinoid compounds such as terpenoids (e.g., β-myrcene, β-caryophyllene, limonene, linalool, pulegone, 1,8-cineole, α-pinene, α-terpineol, terpinen-4-ol, 4-terpineol, p-cymene, borneol, Δ3-carene), flavonoids (e.g., apigenin, quercetin, cannflavin A), phytosterols (e.g., β-sitosterol), and others. The present compositions contain a noticeably greater amount of terpenoids, far exceeding any previous method to date.

In some embodiments of the present process, the crude *Cannabis* extract is mixed in a solvent such as ethanol or isopropyl alcohol until dissolved. The crude *Cannabis* extract can be swirled or mixed with a stainless steel utensil until the solids fully dissolved. The mixture is then set in a freezer at temperatures ranging from about 0° C. to about −20° C., for at least 1 hour, alternatively from 24 to 48 hrs. After that period, the mixture is filtered. Then it is immersed in a warm water bath, for example at 20° C.-30° C., or a hot water batch, for example at 105° C.-110° C., for as long as needed to evaporate the solvent. The mixture may be subjected to a low pressure or vacuum environment to assist solvent removal.

The refined *Cannabis* extract can be used in a personal vaporizer, which generates a vapor containing one or more cannabinoid compounds. When vapor is inhaled by a person using a personal vaporizer, the vapor at least enters the person's mouth during usage. Generally the vapor is drawn in as the person breathes, however the vapor may be carried by a propellant. In the present application, "inhale" means any breathe in, draw in, ingest, take into the mouth, trachea, and/or lungs.

Many over-the-counter and other specialty vaporizers use various forms of personal vaporizer liquid. The present liquid compositions could be used in any of those devices, and perhaps others that may be adapted for vaporizing both liquid and non-liquid materials.

The present compositions can include a liquid co-solvent with the refined *Cannabis* extract. The co-solvent can be included in any desired ratio to the refined *Cannabis* extract, so long as the liquid composition remains capable of being vaporized and inhaled. Generally the co-solvent and refined *Cannabis* extract both vaporize within the temperature ranges provided herein. Liquid co-solvents include propylene glycol, glycerol and PEG-400. PEG-400 and glycerol are less effective in dissolving oils, are less compatible with the chosen emulsifiers and are known to produce by-products when vaporized. The types and amounts of liquid base should be selected so that a sufficiently stable emulsion is formed, without the use of self-emulsifying agents that create a range of unstable results.

The liquid composition can included a winterized *cannabis* extract and a co-solvent (such as propylene glycol), in various ratios of co-solvent to *Cannabis* extract. For example, the ratio of co-solvent to winterized *Cannabis* extract can be from about 1:200 to about 200:1, from about 5:1 to about 1:5, alternatively from about 3:1 to about 1:3, alternatively about 1:1. In some embodiments, the liquid composition comprises about 25% by weight of co-solvent and about 75% by weight of winterized *Cannabis* extract; about 50% by weight of co-solvent and about 50% by weight of winterized *Cannabis* extract; or about 75% by weight of co-solvent and about 25% by weight of winterized *Cannabis* extract. In some embodiments, the liquid composition comprises about 25% by weight of co-solvent and about 75% by weight of winterized *Cannabis* extract; about 50% by weight of co-solvent and about 50% by weight of winterized *Cannabis* extract; or about 75% by weight of co-solvent and about 25% by weight of winterized *Cannabis* extract. The foregoing and following weight percentages are based on the weight of the total composition.

Suitable amounts of the co-solvent in a liquid composition include at least about 0.0001% by weight, alternatively at least about 0.001% by weight, alternatively at least about 0.005% by weight, alternatively at least about 0.01% by weight, alternatively at least about 0.02% by weight, alternatively at least about 0.05% by weight, alternatively at least about 0.07% by weight, alternatively at least about 0.1% by weight, alternatively at least about 0.15% by weight, alternatively at least about 0.2% by weight, alternatively at least about 0.25% by weight, alternatively at least about 0.5% by weight, alternatively at least about 0.75% by weight, alternatively at least about 1% by weight, alternatively at least about 1.2% by weight, alternatively at least about 1.4% by weight, alternatively at least about 1.8% by weight, alternatively at least about 2% by weight, alternatively at least about 3% by weight, alternatively at least about 5% by weight. Suitable amounts of the co-solvent in a liquid composition include at most about 95%, alternatively at most about 85%, alternatively at most about 75%, alternatively at most about 50%, alternatively at most about 20%, alternatively at most about 15%, alternatively at most about 10%, alternatively at most about 5%, alternatively at most about 2.5%, alternatively at most about 2%, alternatively at most about 1.5%, alternatively at most about 1%, alternatively at most about 0.75%, alternatively at most about 0.5%, alternatively at most about 0.2%. Any of the foregoing minimums can be combined with any of the foregoing maximums to provide a range, provided that the minimum is less than the maximum. For examples a suitable range is from about 0.01% to about 97.5% by weight, alternatively from about 0.01% to about 99.9% by weight.

The foregoing liquid compositions and methods of use can be used as a base method of use for the vaporization of refined *cannabis* extracts with added components (such as other medicinal agents, flavorants, or other components) to form a stable emulsion suitable for use in a personal vaporizer. The refined *cannabis* extracts are used at the ratio 100:0, mixed together or added to a suitable amount of the co-solvent, 95:5, 75:25, 50:50, 25:75, 5:95, and/or any combination thereof, to form a liquid mixture at any desired range of cannabanoids or extract/co-colvent ratio. In some embodiments, the ratio of co-solvent to *Cannabis* extract is a ratio between 99.95:0.05 and 0.05:99.95, alternatively a ratio between 95:5 and 5:95. The ratios can be based on weight or volume. Stable emulsion is formed within minutes of mixing the refined *cannabis* extract with the co-solvent. There is no heat required for a stable emulsion between winterized extract and co-solvent. It may also be desirable to stir, shake or otherwise agitate the liquid mixture in order to expedite emulsions.

In some embodiments of the present invention, a refined, stable liquid composition, from the "winterization" of crude *Cannabis* extracts, with or without an additional co-solvent, is created for vaporization and inhalation by subject. The refined *Cannabis* extracts and/or mixtures of multiple extracts with or without a co-solvent should be stored in an amber, UV-resistant, glass container, away from sun-light, and stored in moderate conditions for extended shelf-life, or a delivery vessel suitable for a consumer. The liquid compositions may be provided in a vial, cartridge or other container. The stability of the composition may be measured or quantified by a clear composition with no visible waxy ballast, no visible impurities and a liquid form after winterization.

Suitable amounts of the refined *Cannabis* extracts (either individually or collectively where there is more than one) in a liquid composition include at least about 0.001% by weight, alternatively at least about 0.005% by weight, alternatively at least about 0.01% by weight, alternatively at least about 0.02% by weight, alternatively at least about 0.05% by weight, alternatively at least about 0.07% by weight, alternatively at least about 0.1% by weight, alternatively at least about 0.15% by weight, alternatively at least about 0.2% by weight, alternatively at least about 0.25% by weight, alternatively at least about 0.5% by weight, alternatively at least about 0.75% by weight, alternatively at least about 1% by weight, alternatively at least about 1.2% by weight, alternatively at least about 1.4% by weight, alternatively at least about 1.8% by weight, alternatively at least about 2% by weight, alternatively at least about 3% by weight, alternatively at least about 5% by weight. Suitable amounts of the refined *cannabis* extracts (either individually or collectively where there is more than one) in a liquid composition include at most 100%, alternatively at most about 95%, alternatively at most about 90%, alternatively at most about 85%, alternatively at most about 80%, alternatively at most about 75%, alternatively at most about 72.5%, alternatively at most about 70%, alternatively at most about 67.5%, alternatively at most about 65%, alternatively at most about 60%, alternatively at most about 50%, alternatively at most about 40%, alternatively at most about 30%, alternatively at most about 25%, alternatively at most about 20%, alternatively at most about 15%, alternatively at most about 10%, alternatively at most about 5%, alternatively at most about 2.5%, alternatively at most about 2%, alternatively at most about 1.5%, alternatively at most about 1%, alternatively at most about 0.75%, alternatively at most about 0.5%, alternatively at most about 0.2%. Any of the foregoing minimums can be combined with any of the foregoing maximums to provide a range, provided that the minimum is less than the maximum. For examples a suitable range is from about 100% to about 2.5% by weight or volume.

The liquid composition or stable emulsion can include additional components, such as flavorants, humectants, antioxidants and other components.

In some embodiments, the liquid composition could include one or more flavorants. The term "flavorant" as used herein refers to a compound that provides a desired taste and/or smell when vaporized. The flavorant can be a natural or artificial compound, and it can, but does not have to be, oil-soluble. Flavorants include isoamyl acetate (or other banana flavorant), benzaldehyde (or other almond flavorant), cinnamic aldehyde (or other cinnamon flavorant), citric acid or ethyl propionate (or other fruity flavorant), methyl anthranilate (or other grape flavorant), limonene (or other orange flavorant), ethyl decadienoate (or other pear flavorant), allyl hexanoate (or other pineapple flavorant), ethyl maltol (or other sugar or cotton candy flavorant), ethylvanillin (or other vanilla flavorant), methyl salicylate (or other wintergreen flavorant), glyceryl monoacetate (E1516 food additive), glyceryl diacetate (E1517 food additive), and combinations thereof.

Additional components that may be included in the liquid composition or stable emulsion are taurine, caffeine, glucuronolactone, tryptophan, gamma-aminobutyric acid, melatonin, epimedium, yohimbine, and others.

Suitable humectants include glyceryl triacetate (E1518 food additive).

The present compositions and methods can be used for treating various diseases, disorders or conditions. For example, it is contemplated that the present compositions and methods, when the composition includes one or more refined *cannabis* extracts, as well as synthetic cannabinoid compounds or other medicinal agents can be used for treating pain such as cancer pain, bone pain, neuropathic pain and others; central nervous system disorders such as psychosis or schizophrenia; autoimmune diseases such as multiple sclerosis, inflammatory bowel disease; withdrawal or relapse from opioid dependence. The term "treating" as used herein can include any of the following: alleviating, reducing, improving, mitigating, or eliminating a disease, disorder or condition.

An exemplary personal vaporizer will have a reservoir for holding the liquid composition to be vaporized, a heater, atomizer, nebulizer or other means for vaporizing in fluid connection with the reservoir, a power source such as a battery that provides power to the heater, atomizer, nebulizer or other means when activated, a vapor chamber where vapor is formed, a mouthpiece for a subject to inhale from the personal vaporizer, and a pathway from the vapor chamber to the mouthpiece. The vapor chamber and the reservoir may be separate spaces or may be the same space in the personal vaporizer. When the personal vaporizer is activated, the liquid composition in the reservoir is vaporized, and the user provides suction by inhalation to inhale the vaporized liquid composition.

The liquid composition can be loaded into the personal vaporizer in any suitable way. For some devices, the liquid composition will be poured into a reservoir of the personal vaporizer. For other devices, a cartridge that is pre-filled with the liquid composition may be attached to the personal vaporizer so as to provide the liquid composition to the reservoir or to the heater, atomizer or nebulizer. In some embodiments, the pre-filled cartridge may be the reservoir for the personal vaporizer.

EXAMPLE 1

In this example, a liquid composition suitable for use as a stock emulsion was prepared in four ratios. The composition was prepared by "winterizing" 100% by weight of crude *cannabis* extract turning it into just over 75% refined *cannabis* extract liquid. Then multiple compositions were prepared containing 25%, 50% & 75% propylene glycol with 75%, 50% & 25% of refined *cannabis* extracts, respectively. The mixture was shaken lightly, and after several minutes, a stable emulsion was formed. The liquids were then poured into storage containers where they have remained stable for 3 months.

The compositions had the performances and terpenoid levels far exceeding current personal vaporizer liquid compositions, comprising *Cannabis* extracts. No thermal decomposition products were detected when the compositions were used in a personal vaporizer, in that no burning or smoking was observed. This entire procedure was repeated more than 30 times with consistent results, with the only variable being the amount of refined *Cannabis* extract after 'winterization' process, resulting from a variety of start material and performance of initial extraction. Potency remained high, as the biologically inactive carboxylic acids remained inactive until use in the personal vaporizer. Without the step of decarboxylation, the potency remains high and shelf-life of products greatly increases.

Example 2

A liquid composition was created by combining two varieties of refined *cannabis* extracts made by winterization at −20° C. for 48 hours. A high-percentage CBD strain, and a high-percentage THC strain were mixed, creating a mixture of pure extracts for vaporization. The liquid composition was formed in less than 5 minutes creating a high-purity, stable liquid composition suitable for a personal vaporizer. The refined extracts were prepared by winterization of two separate crude *cannabis* extracts. The *cannabis* extracts were mixed equally, stabilizing in minutes to form a liquid composition suitable as a personal vaporizer liquid in a pure form with no additional solvent, suspension or emulsifying agents. This personal vapor liquid contained desired amounts of winterized *cannabis* extracts for use in a personal vaporizer.

The liquid composition was created by winterization of crude *cannabis* extract, and the removal of waxy ballast was indicated by a visual clarity test, as well as potency, and an abundance of terpenoids. No thermal decomposition products were detected when the composition was used in a personal vaporizer, in that no burning or smoking was observed, and the taste and potency of the vaporized material was not adversely affected by the process. This procedure was repeated more than 30 times, with consistent results.

All of the references cited herein, including patents, patent applications, and publications, are hereby incorporated in their entireties by reference.

In the present disclosure, wherever the word "comprising" is found, it is contemplated that the words "consisting essentially of" or "consisting of" may be used in its place.

While particular elements, embodiments and applications of the present invention have been shown and described, it will be understood, of course, that the invention is not limited thereto since modifications can be made by those skilled in the art without departing from the scope of the present disclosure, particularly in light of the foregoing teachings.

What I claim is:

1. A personal vaporizer with a vapor chamber containing a liquid composition consisting essentially of a *cannabis* extract and glyceryl triacetate.

2. The personal vaporizer of claim 1, wherein the *cannabis* extract is a winterized *cannabis* extract.

3. A container holding a liquid composition consisting essentially of a *cannabis* extract and glyceryl triacetate, wherein the container is adapted for attachment to a personal vaporizer.

4. The container of claim 3, wherein the *cannabis* extract is a winterized *cannabis* extract.

* * * * *